United States Patent [19]

Campbell

[11] 4,279,910

[45] Jul. 21, 1981

[54] QUINAZOLINE THERAPEUTIC AGENTS

[75] Inventor: Simon F. Campbell, Deal, England

[73] Assignee: Pfizer Inc., New York, N.Y.

[21] Appl. No.: 140,534

[22] Filed: Apr. 15, 1980

[30] Foreign Application Priority Data

Apr. 25, 1979 [GB] United Kingdom ............... 14431/79

[51] Int. Cl.³ .................. A61K 31/505; C07D 403/04
[52] U.S. Cl. ...................................... 424/251; 544/291
[58] Field of Search ........................ 544/291; 424/251

[56] References Cited

U.S. PATENT DOCUMENTS

| | | | |
|---|---|---|---|
| 3,511,836 | 5/1970 | Hess | 544/291 |
| 4,001,237 | 1/1977 | Partyka et al. | 544/291 |
| 4,026,894 | 5/1977 | Winn et al. | 544/291 |

FOREIGN PATENT DOCUMENTS 2646186  4/1977  Fed. Rep. of Germany ........... 544/291
2007656  5/1979  United Kingdom ..................... 544/291

*Primary Examiner*—Paul M. Coughlan, Jr.
*Attorney, Agent, or Firm*—Francis X. Murphy; Charles J. Knuth; Peter C. Richardson

[57] ABSTRACT

A series of novel 4-amino-6,7-di(lower alkoxy)-2-(4-substituted piperazino)quinazoline derivatives have been prepared, including their pharmaceutically acceptable acid addition salts. These derivatives all possess a benzo-oxacycloalkanoyl moiety located at the 4-position of the piperazine ring. Such compounds are useful in therapy as highly potent antihypertensive agents. 4-Amino-2-[4-(chroman-2-carbonyl)piperazino]-6,7-dimethoxyquinazoline represents a typical and preferred member compound. Methods for preparing all these compounds from known starting materials are provided and the principal synthetic route leading to the desired final products is described in some detail.

7 Claims, No Drawings

QUINAZOLINE THERAPEUTIC AGENTS

BACKGROUND OF THE INVENTION

This invention relates to therapeutic agents which are novel derivatives of 4-amino-6,7-di(lower alkoxy)-2-piperazino-quinazoline. These particular compounds are useful as regulators of the cardiovascular system and, in particular, in the treatment of hypertension.

SUMMARY OF THE INVENTION

The novel compounds according to the present invention are those of the general formula:

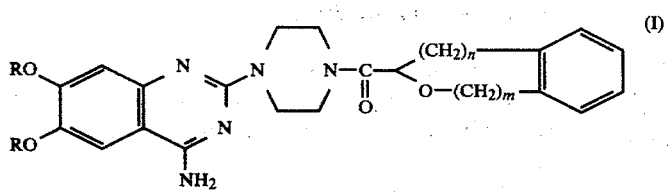

and the pharmaceutically acceptable acid addition salts thereof, wherein R is alkyl having from one to four carbon atoms; and m and n are each zero, one or two, with the proviso that m plus n always equals one or two.

Pharmaceutically acceptable acid addition salts of the compounds of the invention are those salts formed from acids which yield non-toxic acid addition salts containing pharmaceutically acceptable anions, such as the hydrochloride, hydrobromide, sulfate or bisulfate, phosphate or acid phosphate, acetate, maleate, fumarate, succinate, lactate, tartrate, citrate, gluconate, saccharate and p-toluenesulfonate salts.

The invention also includes within its scope various novel pharmaceutical compositions comprising a compound of the formula (I) or a pharmaceutically acceptable acid addition salt thereof, together with a pharmaceutically acceptable carrier or diluent.

In addition, the invention yet further provides a method of treating an animal, including a human being, having hypertension, which comprises administering to said hypertensive animal an effective antihypertensive amount of a compound of the formula (I) or pharmaceutically acceptable acid addition salt thereof, or pharmaceutical composition as hereinafter defined for the present purposes at hand.

DETAILED DESCRIPTION OF THE INVENTION

The compounds of the invention can be prepared by reacting a quinazoline compound of the formula:

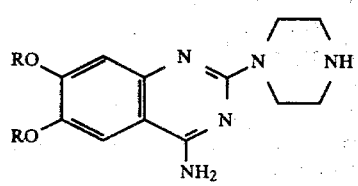

with a carboxylic acid of the formula:

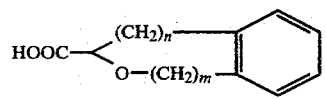

or with its functional equivalent as an acylating agent, e.g., an acid chloride or bromide, an "activated" ester, or a mixed anhydride of the compound of the formula (III).

The acid chlorides or bromides may be prepared by conventional procedures, e.g., by reacting the free acid with, respectively, thionyl chloride or bromide. The preferred activated esters are the succinimido and phthalimido esters which, again, may be prepared by conventional procedures, e.g., by reacting the free acid with N-hydroxysuccinimide in the presence of a dehydrating agent like dicyclohexylcarbodiimide, etc.

Suitable mixed anhydrides, on the other hand, have the formula:

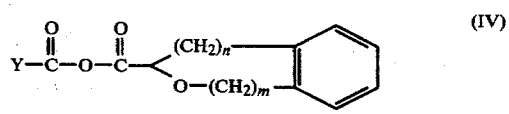

wherein Y is a $C_1$-$C_4$ alkyl group and preferably, it is a tertiary-butyl group. The anhydrides may be prepared by using conventional procedures like reacting the free acid with the appropriate $C_2$-$C_4$ alkanoyl chloride, e.g., pivaloyl chloride, in the presence of a base such as triethylamine.

In practice, if the free acid from the compound of formula (III) is used for preparing the compounds of the invention, the reaction should generally be carried out in the presence of a dehydrating agent such as dicyclohexylcarbodiimide. However, the preferred method for preparing these compounds generally involves the use of an acid chloride of formula (III).

In a typical procedure involving the use of such an acid chloride, a solution of the acid chloride in a suitable solvent, e.g., methylene chloride, is added dropwise to a suspension of the piperazinoquinazoline in a suitable solvent of the same type, with the reaction mixture being cooled throughout the addition step. After stirring at room temperature for a few hours, the resulting solid residue is filtered off and partitioned between, e.g., sodium carbonate solution and chloroform. The chloroform layer can then be evaporated in vacuo and the resulting solid residue subsequently chromatographed on silica gel, for example. After elution with a suitable solvent such as chloroform and then with chloroform-methanol, the appropriate fractions can be combined, evaporated in vacuo and the final residue subsequently recrystallized from a suitable solvent, such as ethyl acetate, to yield the desired pure product.

The piperazinoquinazolines of the formula (II) and the acids of the formula (III) are either known compounds or else they may be easily prepared by using procedures analogous to those of the prior art. For instance, appropriate methods for preparing the compounds of formula (III) are described in Arch. Pharm. (Weinheim), 1966, 299, 931; J. Med. Chem., 1963, 6, 315 and J. Med. Chem., 1968, 11, 844.

The pharmaceutically acceptable acid addition salts of the compounds of the invention can be prepared by conventional procedures, e.g., by reacting the free base with the appropriate acid in an inert organic solvent, and then collecting the resulting precipitate of the salt by means of filtration. If required, the product may then be further crystallized (and recrystallized) in order to achieve complete purification.

The activity of the compounds of the present invention, as antihypertensive agents, is shown by their ability to lower the blood pressure of conscious spontaneously hypertensive rats and conscious renally hypertensive dogs, when administered orally at dose levels of up to 5 mg./kg.

The compounds of the invention can be administered alone, but will generally be administered in admixture with a pharmaceutical carrier selected with regard to the intended route of administration and standard pharmaceutical practice. For instance, they may be administered orally in the form of tablets containing such excipients as starch or lactose, or in capsules either alone or in admixture with excipients, or in the form of elixirs or suspensions containing flavoring or coloring agents. They may also be injected parenterally, for example, intramuscularly, intravenously or subcutaneously. For purposes of parenteral administration, they are best used in the form of a sterile aqueous solution which may contain other solutes like, for example, sufficient saline or glucose to make the solution isotonic.

The compounds of the invention can be administered to humans for the treatment of hypertension by either the oral or parenteral routes, and may be administered orally at dosage levels approximately within the range of 1.0 to 20 mg./day for an average adult patient (70 kg.), given in a single dose of up to three divided doses. Intravenous dosage levels would be expected to be about one-tenth to one-fifth of the daily oral dose, given in a single administration. Thus, for an average adult patient, individual oral doses in tablet or capsule form will be approximately in the range from 1.0 mg. to 20 mg. of active compound. Variations will necessarily occur depending on the weight and condition of the subject being treated and the particular route of administration chosen.

PREPARATION A

Chroman-2-carbonyl chloride (chroman-2-carboxylic acid chloride) was prepared from the known chroman-2-carboxylic acid by reaction of the latter compound with thionyl chloride in accordance with conventional organic procedure.

PREPARATION B 2,3-Dihydrobenzo[b]furan-2-carbonyl chloride (2,3-dihydrobenzo[b]furan-2-carboxylic acid chloride) was prepared from the known 2,3-dihydrobenzo[b]furan-2-carboxylic acid by reaction of the latter compound with thionyl chloride in accordance with conventional organic procedure.

PREPARATION C

Isochroman-1-carbonyl chloride (isochroman-1-carboxylic acid chloride) was prepared from the known isochroman-1-carboxylic acid by reaction of the latter compound with thionyl chloride in accordance with conventional organic procedure.

EXAMPLE 1

A solution consisting of chroman-2-carbonyl chloride (1.13 g.) in dry methylene chloride (20 ml.) was added dropwise to a stirred suspension of 4-amino-6,7-dimethoxy-2-piperazinoquinazoline (1.38 g.) in dry methylene chloride (30 ml.) with ice bath cooling. The resulting reaction mixture was then stirred at room temperature (20° C.) overnight (approximately 16 hours), and the solid product so obtained was subsequently partitioned between aqueous sodium carbonate solution (30 ml., 1.0 N) and chloroform (220 ml.). The chloroform layer which separated was subsequently evaporated in vacuo and the resulting residue (2.5 g.) was thereafter chromatographed on silica gel (100 g.), eluting first with chloroform (200 ml.) and then with chloroform-methanol (800 ml., 97.5:2.5 parts by volume). The appropriate fractions were then collected and subsequently combined and evaporated in vacuo, and the resulting final product thereafter recrystallized from ethyl acetate to give pure 4-amino-2-[4-(chroman-2-carbonyl)piperazino]-6,7-dimethoxyquinazoline (yield, 625 mg.), m.p. 165°-167° C.

Anal. Calcd. for $C_{24}H_{27}N_5O_4$: C, 64.1; H, 6.1; N, 15.6. Found: C, 64.0; H, 6.1; N, 15.4.

EXAMPLE 2

The procedure described in Example 1 was followed except that 2,3-dihydrobenzo[b]furan-2-carbonyl chloride was the acylating agent of choice employed instead of chroman-2-carbonyl chloride, using the same molar proportions as before. In this particular case, the corresponding final product obtained (i.e., the product isolated after completion of the chromatographic purification step) was later taken up in chloroform and treated with ethereal hydrogen chloride to ultimately afford pure 4-amino-6,7-dimethoxy-2-[4-(2,3-dihydrobenzo[b]furan-2-carbonyl)piperazino]-quinazoline hydrochloride hemihydrate, m.p. 280°-280.5° C.

Anal. Calcd. for $C_{23}H_{25}N_5O_4 \cdot HCl \cdot 0.5H_2O$: C, 57.4; H, 5.7; N, 14.6. Found: C, 57.5; H, 5.5; N, 14.5.

EXAMPLE 3

The procedure described in Example 2 was repeated except that isochroman-1-carbonyl chloride was the acylating agent of choice employed instead of chroman-2-carbonyl chloride, using the same molar proportions as before. In this particular case, the corresponding final product thus obtained was ultimately pure 4-amino-6,7-dimethoxy-2-[4-(isochroman-1-carbonyl)piperazino]-quinazoline hydrochloride hydrate, m.p. 281°-282° C.

Anal. Calcd. for $C_{24}H_{27}N_5O_4 \cdot HCl \cdot H_2O$: C, 57.2; H, 6.0; N, 14.0. Found: C, 57.2; H, 5.6; N, 14.2.

I claim:

1. A compound of the formula:

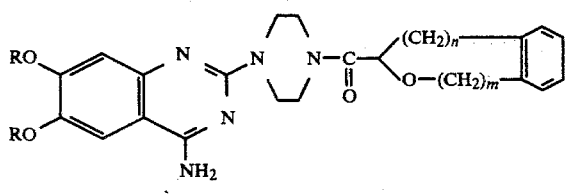

and the pharmaceutically acceptable acid addition salts thereof, wherein R is alkyl having from one to four carbon atoms; and m and n are each zero, one or two, with the proviso that m plus n always equals one or two and when m is zero, n is 2.

2. A compound as claimed in claim 1 wherein R is methyl.

3. A compound as claimed in claim 2 wherein m is zero and n is two.

4. A compound as claimed in claim 2 wherein m is two and n is zero.

5. 4-Amino-2-[4-(chroman-2-carbonyl)piperazino]-6,7-dimethoxyquinazoline.

6. A method for lowering blood pressure in the treatment of a hypertensive subject, which comprises administering to said subject an effective amount of a compound as claimed in claim 1.

7. A pharmaceutical composition suitable for oral or parenteral administration comprising a pharmaceutically acceptable carrier and an effective antihypertensive amount of a compound as claimed in claim 1.

* * * * *